(12) United States Patent
Zhang

(10) Patent No.: US 9,422,585 B2
(45) Date of Patent: Aug. 23, 2016

(54) PHYTOGLYCOGEN-BASED COMPOSITIONS, MATERIALS AND METHODS

(71) Applicant: Phytoption, LLC, West Lafayette, IN (US)

(72) Inventor: Jingmin Zhang, West Lafayette, IN (US)

(*) Notice: Subject to any disclaimer, the term of this patent is extended or adjusted under 35 U.S.C. 154(b) by 128 days.

(21) Appl. No.: 14/351,812

(22) PCT Filed: Oct. 15, 2012

(86) PCT No.: PCT/US2012/060249
§ 371 (c)(1),
(2) Date: Apr. 14, 2014

(87) PCT Pub. No.: WO2013/056227
PCT Pub. Date: Apr. 18, 2013

(65) Prior Publication Data
US 2014/0303365 A1    Oct. 9, 2014

Related U.S. Application Data

(60) Provisional application No. 61/547,270, filed on Oct. 14, 2011.

(51) Int. Cl.
| | |
|---|---|
| *A61K 31/718* | (2006.01) |
| *C08B 37/18* | (2006.01) |
| *C12P 19/04* | (2006.01) |
| *C08B 37/02* | (2006.01) |
| *A23L 1/035* | (2006.01) |
| *A23L 1/10* | (2006.01) |
| *A23L 1/105* | (2006.01) |
| *A61K 9/107* | (2006.01) |
| *A61K 8/66* | (2006.01) |
| *A61K 8/73* | (2006.01) |
| *A61Q 19/00* | (2006.01) |
| *A61K 8/97* | (2006.01) |
| *A23L 1/30* | (2006.01) |
| *C08B 37/00* | (2006.01) |

(52) U.S. Cl.
CPC ............... *C12P 19/04* (2013.01); *A23L 1/035* (2013.01); *A23L 1/1025* (2013.01); *A23L 1/1055* (2013.01); *A23L 1/3002* (2013.01); *A61K 8/66* (2013.01); *A61K 8/73* (2013.01); *A61K 8/97* (2013.01); *A61K 9/107* (2013.01); *A61K 31/718* (2013.01); *A61Q 19/00* (2013.01); *C08B 37/0009* (2013.01); *C08B 37/0021* (2013.01); *C08B 37/18* (2013.01); *A23V 2200/00* (2013.01); *A61K 2800/10* (2013.01)

(58) Field of Classification Search
None
See application file for complete search history.

(56) References Cited

U.S. PATENT DOCUMENTS 5,895,686 A * 4/1999 Horino .................... A23L 1/052
426/459
2008/0131941 A1 6/2008 Kajiura et al.

FOREIGN PATENT DOCUMENTS

WO    2011062999 A2    5/2011

OTHER PUBLICATIONS

Inouchi et al., "Development Changes in Fine Structure of Starches of Several Endosperm Mutants of Maize" Starch/Starke (1983) vol. 35 No. 11, pp. 371-376.*
Wong et al., "Structures and Properties of Amylopectin and Phytoglycogen in the Endosperm of sugary-1 Mutants of Rice" Journal of Cereal Science (2003) vol. 37 pp. 139-149.*
Syahariza et al., "Extraction and dissolution of starch from rice and sorghum grains for accurate structural analysis" Carbohydrate Polymers (2010) vol. 82 pp. 14-20.*
Bi et al., "Designing carbohydrate nanoparticles for prolonged efficacy of antimicrobial peptide", Journal of Controlled Relsease, 2011, vol. 150, pp. 150-156.
Bi et al., "Carbohydrate Nanoparticle-Mediated Colloidal Assembly for Prolonged Efficacy of Bacteriocin Against Food Pathogen", Biotechnology, and Bioengineering, 2011, vol. 108, pp. 1529-1536.
Huang et al., "Particulate structure of phytoglycogen nanoparticles probed using amyloglucosidase", Carbohydrate Polymers, 2011, vol. 83, pp. 1665-1671.
Scheffler et al., "In Vitro Digestibility and Emulsification Properties of Phytoglycogen Octenyl Succinate", Journal of Agricultural and Food Chemistry, 2010, vol. 58, pp. 5140-5146.
Scheffler et al., "Phytoglycogen Octenyl Succinate, an Amphiphilic Carbohydrate Nanoparticle, and ϵ-Polylysine to Improve Lipid Oxidative Stability of Emulsions", Journal of Agricultural and Food Chemistry, 2010, vol. 58, pp. 660-667.
Shin et al., "Glucose Release of Water-Soluble Starch-Related α-Glucans by Pancreatin and Amyloglucosidase Is Affected by the Abundance of α-1,6-Glucosidic Linkages", Journal of Agricultural and Food Chemistry, 2008, vol. 56, pp. 10879-10886.
PCT International Search Report and the Written Opinion, Application No. PCT/US2012/060249 filed Oct. 15, 2012, dated Feb. 25, 2013.
PCT International Preliminary Report on Patentability, Application No. PCT/US2012/060249 filed Oct. 15, 2012, dated Apr. 15, 2014.

* cited by examiner

*Primary Examiner* — Eric Olson
(74) *Attorney, Agent, or Firm* — MacMillan, Sobanksi & Todd, LLC

(57) ABSTRACT

The present invention provides methods for treating phytoglycogen-containing materials to generate phytoglycogen compositions with enhanced emulsification attribute. One method comprises contacting a phytoglycogen-containing material with at least one protease. The other method comprises heat treatment of a phytoglycogen-containing material, such as corn kernels. The two methods can be applied independently, or can be applied in combination. Applications of phytoglycogen compositions are also included.

24 Claims, 4 Drawing Sheets

PHYTOGLYCOGEN-BASED COMPOSITIONS, MATERIALS AND METHODS

CROSS REFERENCE TO RELATED APPLICATIONS

Figure 1:
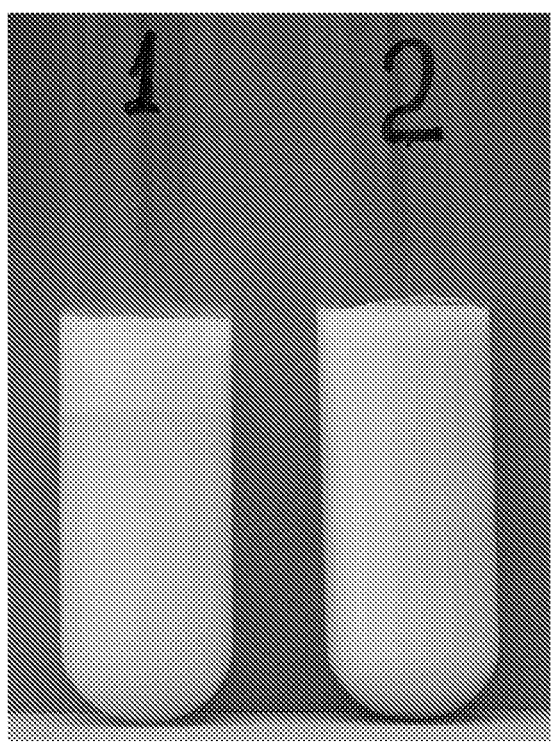

This application claims the benefit of PCT application No. PCT/US2012/060249 filed Oct. 15, 2012, which claims priority to U.S. Provisional Application No. 61/547,270 filed Oct. 14, 2011, the disclosure of which is incorporated herein by reference.

STATEMENT REGARDING FEDERALLY SPONSORED RESEARCH

This invention was not made with government support.

TECHNICAL FIELD OF THE INVENTION

The present invention relates to phytoglycogen-based emulsifiers, compositions comprising the emulsifiers, and their preparation and use.

BACKGROUND OF THE INVENTION

Plant-derived glycogen, or "phytoglycogen" is a highly branched water-soluble polymer of glucosyl units. Plants utilize the plant polysaccharide in the same manner animals utilize glycogen: as energy for metabolic processes. A number of plants produce phytoglycogen, including corn, rice, *sorghum*, barley, and *Arabidopsis*. Phytoglycogen exists in particulate sizes of approximately 40 to 50 nm.

Plant starch biosynthesis depends on starch synthases, branching enzymes, and debranching enzymes. In the absence of debranching enzyme activity, phytoglycogen is formed instead of starch. In corn, a mutation in the "sugary 1" gene (su1) results in a deficiency of an isoamylase-type debranching enzyme, SU1. SU1-dysfunctional corn kernels are sweeter than varieties with functional SU1, due to an overabundance of phytoglycogens and accumulation of sugars.

The highly branched structure of phytoglycogen contributes to its unusually high molecular density when in dispersion. The dispersed molecular density of corn phytoglycogen is about 1200 $g/mol/nm^3$, compared with about 60 $g/mol/nm^3$ for amylopectin of starch. The natural density and branching of phytoglycogen promotes structural integrity and supports functional group grafting at the surface.

With regard to the polymer structure, phytoglycogen does not possess long chains that connect individual clusters, as does amylopectin. It is likely that phytoglycogen particulates grow from the non-reducing ends of glucan chains at the surface, by periodic branching and elongation of glucan chains.

Others have modified phytoglycogen for various purposes. For example, Scheffler et al. reported a procedure in which phytoglycogen was contacted with octenyl succinic anhydride (OSA) to yield phytoglycogen octenyl succinate (PG-OS). PG-OS showed an outstanding property to form oil-in-water emulsion after homogenization. Scheffler et al., *J of Ag and Food Chem,* 58: 5140-514 (2010) and Scheffler et al., *J of Ag and Food Chem,* 58: 660-667 (2010).

Bi et al. also reported procedures for reacting phytoglycogen with OSA or succinic anhydride (SA), yielding PG-OS and phytoglycogen succinate (PG-S) with various degree of substitution. These chemically modified phytoglycogen materials were further tested for their capability to adsorb antimicrobial peptide, such as nisin for prolonged antimicrobial effects against food pathogens such as *Listeria monocytogenes*. Bi et al., *Biotech and Bioengineering,* 108: 1529-1536 (2011) and Bi et al., *J of Controlled Release,* 150: 150-156 (2011).

In these reports, however, chemical substitutions were used to bring functionalities to phytoglycogen materials. This not only increases the cost of products, but also is unsuitable for the natural and "green" formulations that are highly pursued by the industry and consumers.

Previously-known food emulsifiers include proteins (e.g. casein, whey protein, and soybean proteins), small-molecule surfactants (e. g. lecithin, sorbitan esters, sugar esters, and monoglyceride), and polysaccharide-based materials (e.g. gum Arabic, starch octenyl succinates, and hemicellulose). The primary use of these emulsifiers is to stabilize oil-in-water or water-in-oil droplets by forming a stable interfacial layer. For the purpose of encapsulation, the emulsions (usually the oil-in-water emulsions) are converted to a solid form by methods such as spray drying or freeze drying. Usually the wall materials or bulking agents are needed for encapsulation to form a protective layer over the oil droplets. Biopolymers, particularly those with low viscosity at higher concentrations, such as maltodextrin are suitable as wall materials. Gum Arabic and starch octenyl succinate (starch-OSA), both having emulsification and bulking properties, are suitable for encapsulation.

Starch-OSA is chemically modified, which limits label claims desired by the food industry. Hemicellulose has high cost and high viscosity that hinders its applications in encapsulation.

Protein-based emulsifiers are broadly used; however, they have disadvantages of high cost and low heat stability in food processing.

While polysaccharide-based emulsifiers can form stable emulsions, there are limitations for their applications. For example, gum Arabic faces the challenge of high cost due to scarcity of this material.

Therefore, there is a strong need for methods for preparing natural and functional emulsifiers without using chemical modifications.

SUMMARY OF THE INVENTION

The present invention provides phytoglycogen compositions, wherein the phytoglycogen compositions are characterized by their emulsification attributes, that is, their capabilities to form and/or enhance emulsions.

In this invention, the enhanced emulsion stability is characterized by enhanced quality of emulsion to show: reduced or negligible formation of cream layers; reduced or negligible layer separation; reduced or negligible flocculation or coalescence; and/or by increased homogeneity of emulsion after emulsification and during storage.

In this invention, a stable emulsion is characterized as an emulsion that shows: 1) unobservable or negligible cream layer formation, layer separation, flocculation, and/or coalescence, and 2) overall homogeneity during storage.

The stability of emulsion is defined as the duration in which the emulsion remains stable at a given environmental condition (e.g. temperature). Higher stability of emulsion is characterized by longer duration of emulsion to remain stable. For example, if the duration in which an emulsion is stable is improved for 5 minutes to 10 minutes under the same conditions, then the improvement of emulsion stability is 100% (that is, [(10 minutes–5 minutes)/(5 minutes)] *100%=100%.

The inventor has shown that phytoglycogen composition can be generated to improve emulsion stability by tens or hundreds of times compared with the emulsion system that does not contain the said phytoglycogen composition.

The present invention provides methods for making a phytoglycogen composition with at least one emulsification attribute, comprising contacting a phytoglycogen-containing material with at least one protease under conditions sufficient to obtain a phytoglycogen material having at least one emulsification attribute.

Also provided are those methods wherein the at least emulsification attribute exists either by the phytoglycogen composition alone, or in conjunction with other emulsifier.

Also provided are those methods wherein the at least one emulsification attribute is selected from a group consisting of: unobservable or negligible cream layer formation; unobservable or negligible layer separation; unobservable or negligible flocculation; unobservable or negligible coalescence; and/or overall homogeneity during storage.

Also provided are those methods wherein the at least one emulsification attribute is that the emulsion is stable for at least a number of minutes selected from the group consisting of: 10, 20, 30, 40, 50, 60, 70, 80, 90, 100, 120, 130, 140, 150, 160, 170, 180.

Also provided are those methods wherein the at least one emulsification attribute is that the emulsion is stable for at least a number of hours selected from the group consisting of: 1, 2, 3, 4, 5, 6, 7, 8, 9, 10, 11, 12, 13, 15, 16, 17, 18, 19, 20, 21, 22, 23 and 24.

Also provided are those methods wherein the at least one emulsification attribute is that the emulsion is stable for at least a number of days selected from the group consisting of: 1, 1.5, 2. 2.5, 3, 3.5, 4, 4.5, 5, 5.5, 6, 6.5, and 7.

Also provided are those methods wherein the at least one emulsification attribute is the stability of emulsion formed by treated phytoglycogen material higher than the stability of emulsion formed by untreated control phytoglycogen material, wherein said stability increase percentage is selected from a group consisting of at least about: 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, 1500%, 2000%, 2500%, 3000%, 3500%, 4000%, 4500%, 5000%, 5500%, 6000%, 6500%, 7000%, 7500%, 8000%, 8500%, 9000%, 9500%, 10000%, 20000%.

Also provided are those methods wherein processing conditions comprise temperature ranges selected from the group consisting of these temperature ranges: 5° C. to 90° C.; 30° C. to 70° C.; 30° C. to 50° C.; 35° C. to 45° C.; approximately 40° C.

Also provided are those methods wherein processing conditions comprise time ranges selected from the group consisting of these time ranges: 0.1 to 50 hours; 0.5 hour to 5 hours; 1 hour to 4 hours; 1.5 hour to 3 hours; 1.75 hour to 2.75 hours; approximately 2 hours.

Also provided are those methods wherein processing conditions comprise these pH ranges: pH 3 to pH 12; pH 5 to pH 10; approximately pH 6 to pH 9.

Also provided are those methods wherein processing conditions comprise optimization for protease/phytoglycogen interaction.

Also provided are those methods wherein processing conditions comprise these other variables: protease 0.0001% to 20% (w/w) of substrate phytoglycogen material; temperature 5° C. to 90° C., reaction time 0.1 to 50 hours, pH 3-12.

Also provided are those methods wherein the protease is selected from the group consisting of: plant-derived proteolytic enzyme and peptide hydrolase such as bromelain and papain; animal-derived proteolytic enzyme and peptide hydrolase such as pancreatin, pepsin, trypsin, and rennet; bacterially derived proteolytic enzyme and peptide hydrolase such as aminopeptidase, subtilisin, acid protease, neutral proteinase, and alkaline protease.

Also provided are those methods wherein the treatment is for increased emulsion stability.

Also provided are those methods wherein the phytoglycogen-containing material is an extract from a plant selected from the group consisting of: corn; rice; barley; and *sorghum*.

Also provided are those methods wherein the phytoglycogen is a corn phytoglycogen.

Also provided are those methods wherein the phytoglycogen is a sweet corn phytoglycogen.

Also provided are those methods wherein the phytoglycogen-containing material is an extract of phytoglycogen from heat-treated corn kernels.

Also provided are those methods wherein the phytoglycogen-containing material is an extract of phytoglycogen from heat-treated sweet corn kernels.

Also provided are those methods wherein the phytoglycogen-containing material is derived from at least one corn kernel selected from the group consisting of: degermed corn kernel; degermed sweet corn kernel; non-degermed corn kernel; non-degermed sweet corn kernel; sugary-1 mutant corn kernel; heat-treated corn kernel; heat-treated sweet corn kernel; heat-treated sugary-1 mutant corn kernel.

Also provided are those methods wherein the phytoglycogen-containing material is obtained by:

a.) grinding kernels of a sweet corn containing sugary-1 (su1) mutant alleles;

b.) soaking the ground kernels of step a.) in water;

c.) homogenizing the kernels and water of step b.) so as to disperse the phytoglycogen;

d.) filtering the kernels and water of step c.) so as to remove insoluble solids and oil;

e.) centrifuging the kernels and water of step d.) so as to remove insoluble solids and oil.

Also provided are those methods, which further comprises additional purification of the phytoglycogen-containing material by:

f.) adding solvent to precipitate phytoglycogen from other soluble compounds; or g.) ultrafiltration to remove soluble small molecules.

Also provided are those methods which further comprise a second treatment selected from the group consisting of: spray drying; freeze drying; drum drying; chemical substitution; emulsifying; and ingredient use.

The present invention provides methods for making a phytoglycogen composition with emulsification attributes, comprising subjecting a phytoglycogen-containing material to at least one heat treatment under conditions sufficient to obtain a phytoglycogen composition having at least one emulsification attribute.

Also provided are those methods wherein the at least one emulsification attribute exists either by the phytoglycogen composition alone, or in conjunction with other emulsifier.

Also provided are those methods wherein the at least one emulsification attribute is selected from a group consisting of: unobservable or negligible cream layer formation; unobservable or negligible layer separation; unobservable or negligible flocculation; unobservable or negligible coalescence; and/or overall homogeneity during storage.

Also provided are those methods wherein the at least one emulsification attribute is that the emulsion is stable at room temperature for at least a number of minutes selected from the group consisting of: 10, 20, 30, 40, 50, 60, 70, 80, 90, 100, 120, 130, 140, 150, 160, 170, and 180.

Also provided are those methods wherein the at least one emulsification attribute is that the emulsion is stable for at least a number of hours selected from the group consisting of: 1, 2, 3, 4, 5, 6, 7, 8, 9, 10, 11, 12, 13, 15, 16, 17, 18, 19, 20, 21, 22, 23 and 24.

Also provided are those methods wherein the at least one emulsification attribute is that the emulsion is stable for at least a number of days selected from the group consisting of: 1, 1.5, 2. 2.5, 3, 3.5, 4, 4.5, 5, 5.5, 6, 6.5, and 7.

Also provided are those methods wherein the at least one emulsification attribute is the stability of emulsion formed by treated phytoglycogen composition higher than the stability of emulsion formed by untreated control phytoglycogen-containing material, wherein said stability increase percentage is selected from a group consisting of at least about: 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, 1500%, 2000%, 2500%, 3000%, 3500%, 4000%, 4500%, 5000%, 5500%, 6000%, 6500%, 7000%, 7500%, 8000%, 8500%, 9000%, 9500%, 10000%, 20000%.

Also provided are those methods wherein the phytoglycogen-containing material is a plant part.

Also provided are those methods wherein the phytoglycogen-containing material is a seed.

Also provided are those methods, wherein the phytoglycogen-containing material is a corn kernel.

Also provided are those methods wherein the phytoglycogen-containing material is heat treated when the material moisture content is from approximately 0% to 40%.

Also provided are those methods wherein the phytoglycogen-containing material is heat treated when the material moisture content is from approximately 2% to 20%.

Also provided are those methods wherein the phytoglycogen-containing material is heat treated for at least approximately 5 seconds, to at least approximately 300 days.

Also provided are those methods wherein the phytoglycogen-containing material is heat treated for at least approximately 4 hours, to at least approximately 24 hours.

Also provided are those methods wherein the phytoglycogen-containing material is heat treated at a temperature of at least approximately 30° C. to 300° C.

Also provided are those methods wherein the phytoglycogen-containing material is heat treated at a temperature of approximately 110° C.

Also provided are those methods which further comprise subjecting the phytoglycogen-containing material to protease treatment.

Also provided are those methods wherein the method results in a phytoglycogen composition that is capable of increasing emulsion stability.

Also provided are those methods which further comprise a second treatment selected from the group consisting of: spray drying; freeze drying; drum drying; chemical substitution; emulsifying; and ingredient use.

The present invention provides phytoglycogen compositions made by a method herein.

The present invention also provides emulsified products comprising a phytoglycogen herein.

The present invention provides phytoglycogen compositions comprising at least one emulsification attribute.

Also provided are such compositions wherein the at least one emulsification attribute exists either with the phytoglycogen composition alone, or in conjunction with other emulsifier.

Also provided are such compositions wherein the at least one emulsification attribute is selected from a group consisting of: unobservable or negligible cream layer formation; unobservable or negligible layer separation; unobservable or negligible flocculation; unobservable or negligible coalescence; and/or overall homogeneity during storage.

Also provided are such compositions wherein the composition is in the form selected from the group consisting of: a microparticle; a powder; a granule; a solid; a liquid; a semi-solid; an emulsion; a mixture; a coating; a packaging material; and a cake.

Also provided are such compositions wherein the at least one emulsification attribute is selected from a group consisting of: unobservable or negligible cream layer formation; unobservable or negligible layer separation; unobservable or negligible flocculation; unobservable or negligible coalescence; and/or overall homogeneity during storage.

Also provided are such compositions wherein the at least one emulsification attribute is that the emulsion is stable for at least a number of minutes selected from the group consisting of: 10, 20, 30, 40, 50, 60, 70, 80, 90, 100, 120, 130, 140, 150, 160, 170, 180.

Also provided are such compositions wherein the at least one emulsification attribute is that the emulsion is stable for at least a number of hours selected from the group consisting of: 1, 2, 3, 4, 5, 6, 7, 8, 9, 10, 11, 12, 13, 15, 16, 17, 18, 19, 20, 21, 22, 23 and 24.

Also provided are such compositions wherein the at least one emulsification attribute is that the emulsion is stable for at least a number of days selected from the group consisting of: 1, 1.5, 2. 2.5, 3, 3.5, 4, 4.5, 5, 5.5, 6, 6.5, and 7.

Also provided are such compositions wherein the at least one emulsification attribute is the stability of emulsion formed by treated phytoglycogen material higher than the stability of emulsion formed by untreated control phytoglycogen material, wherein said stability increase percentage is selected from a group consisting of at least about: 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, 1500%, 2000%, 2500%, 3000%, 3500%, 4000%, 4500%, 5000%, 5500%, 6000%, 6500%, 7000%, 7500%, 8000%, 8500%, 9000%, 9500%, 10000%, 20000%.

The present invention also provides products comprising a phytoglycogen composition herein.

Also provided are such products which further comprise at least one additional ingredient selected from the group consisting of: an emulsifier, a stabilizer, a liquid.

Also provided are such products selected from the group consisting of: a food, a food ingredient, food packaging, or food-related product.

Also provided are such products selected from the group consisting of: beverage; beverage mix; ready-to-eat cereal; ready-to-eat snack piece; nutritional supplement; flavor and fragrance; dairy product; confection; baked good; soup; topping; sauce; processed meat product; vegetarian product; frozen food; coating materials; encapsulation materials; micro-encapsulation materials; packaging materials; antimicrobial materials; anti-oxidation materials; and edible decoration Also provided are such products which are cosmetics.

Also provided are such products selected from the group consisting of: foundation; eyeliner; rouge; wrinkle modifier; blemish concealer; nail product; skin colorant; mask; lipstick; and mascara.

Also provided are such products which are lotions.

Also provided are such products selected from the group consisting of: moisturizer; sunscreen; anti-wrinkle lotion; antibiotic lotion; muscle pain lotion; foot cream; body lotion; medical lotion; hand cream; and stretch mark cream.

Also provided are such products which are hair treatments.

Also provided are such products selected from the group consisting of: shampoo; conditioner; cream rinse; shining product; holding product; color product; straightening product; and curling product.

Also provided are such products which are pharmaceuticals.

Also provided are such products selected from the group consisting of: a capsule; tablet; liquid; gel; ointment; intravenous formulation; lotion; transdermal delivery formulation; toothpaste; dental treatment; inhalant; and injectable.

Also provided are such products which are agricultural chemicals.

Also provided are such products selected from the group consisting of: a fertilizer; plant nutrient; plant food; herbicide; fungicide; pesticide; biocide; hormone; seed coating; plant coating; soil treatment material; leaf coating; grain processing material; grain storage material; insect repelling material; and antimicrobial material.

Also provided are such products wherein the at least one emulsification attribute is selected from a group consisting of: unobservable or negligible cream layer formation; unobservable or negligible layer separation; unobservable or negligible flocculation; unobservable or negligible coalescence; and/or overall homogeneity during storage of an emulsion.

Also provided are such products wherein the at least one emulsification attribute is that the emulsion is stable for at least a number of minutes selected from the group consisting of: 10, 20, 30, 40, 50, 60, 70, 80, 90, 100, 120, 130, 140, 150, 160, 170, 180.

Also provided are such products wherein the at least one emulsification attribute is that the emulsion is stable for at least a number of hours selected from the group consisting of: 1, 2, 3, 4, 5, 6, 7, 8, 9, 10, 11, 12, 13, 15, 16, 17, 18, 19, 20, 21, 22, 23 and 24.

Also provided are such products wherein the at least one emulsification attribute is that the emulsion is stable for at least a number of days selected from the group consisting of: 1, 1.5, 2. 2.5, 3, 3.5, 4, 4.5, 5, 5.5, 6, 6.5, and 7.

Also provided are such products wherein the at least one emulsification attribute of the product comprising phytoglycogen composition is higher than the stability of controlled product without phytoglycogen composition, wherein said stability increase percentage is selected from a group consisting of at least about: 30%, 40%, 50%, 60%, 70%, 80%, 90%, 100%, 150%, 200%, 250%, 300%, 350%, 400%, 450%, 500%, 550%, 600%, 650%, 700%, 750%, 800%, 850%, 900%, 950%, 1000%, 1500%, 2000%, 2500%, 3000%, 3500%, 4000%, 4500%, 5000%, 5500%, 6000%, 6500%, 7000%, 7500%, 8000%, 8500%, 9000%, 9500%, 10000%, 20000%.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

It must be noted that as used herein and in the appended claims, the singular forms "a", "and", and "the" include plural referents unless the context clearly dictates otherwise. Thus, for example, reference to "a polymorphism" includes a plurality of such polymorphisms, reference to "a nucleic acid molecule" includes a plurality of such nucleic acid molecules, and reference to "the method" includes reference to one or more methods, method steps, and equivalents thereof known to those skilled in the art, and so forth.

BRIEF DESCRIPTIONS OF THE FIGURES

FIG. 1: Comparison of emulsion stability after 9 days of storage in a refrigerator (4° C.). Emulsion-1, emulsion formed by phytoglycogen extraction from non-heat treated, degermed sweet corn kernels; Emulsion-2, emulsion formed by phytoglycogen extraction from heat treated (4 hours, 110° C.), degermed sweet corn kernels. Emulsion-1 shows clear layer separation, indicating a low stability of emulsion. Emulsion-2 shows a homogenous nature of liquid, indicating a high stability of emulsion.

Figure 2:
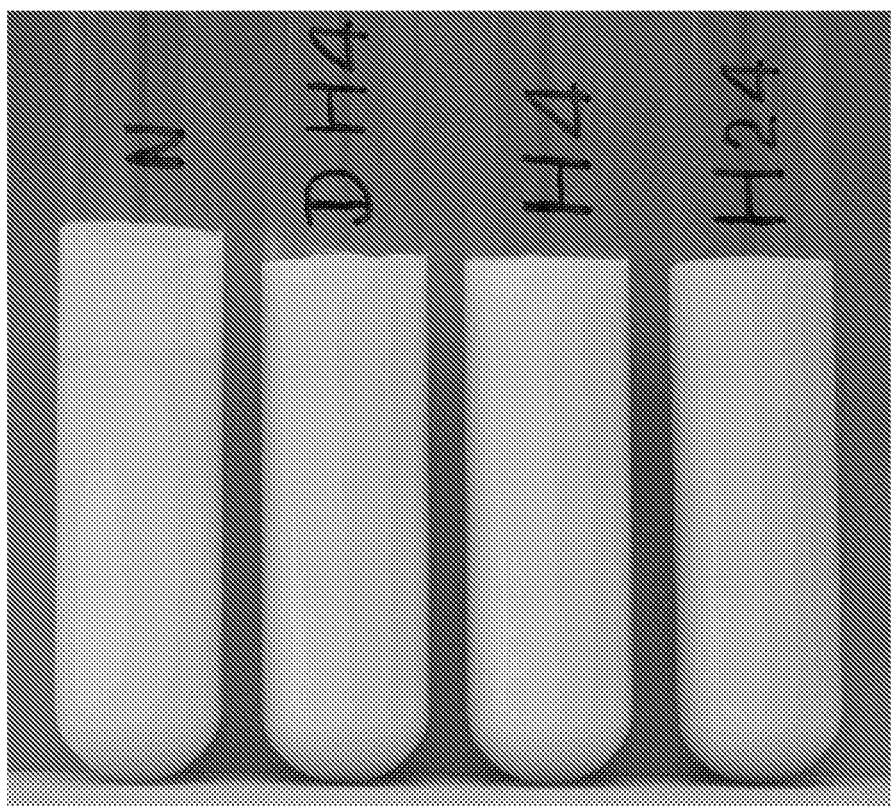

FIG. 2: Comparison of emulsion stability after storage in a refrigerator (4° C.). Emulsion-N, emulsion formed by phytoglycogen extraction from non-heat treated, non-degermed sweet corn kernels, stored for 5 days; Emulsion-DH4, emulsion formed by phytoglycogen extraction from heat-treated (4 hours, 110° C.), degermed sweet corn kernels (DH4 and emulsion-1 in FIG. 1 were aliquots from the same preparation described in Example 10), stored for 9 days; Emulsion-H4, emulsion formed by phytoglycogen extraction from heat-treated (4 hours, 110° C.), non-degermed sweet corn kernels, stored for 5 days; Emulsion-H24, emulsion formed by phytoglycogen extraction from heat-treated (24 hours, 110° C.), non-degermed corn kernels, stored for 5 days. Emulsion-N shows clear layer separation, indicating a low stability of emulsion. Emulsion-DH4, H4, and H24 all show a homogenous nature of liquid, indicating a high stability of emulsions.

Figure 3:
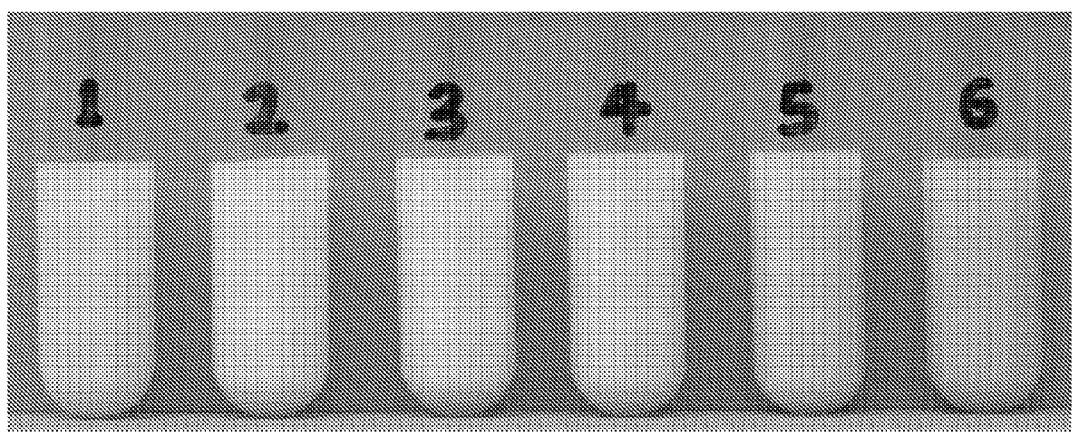

FIG. 3: Re-hydrated, spray dried phytoglycogen (No. 1 and 6) and phytoglycogen-stabilized emulsions (No. 2-5). For each sample, the following liquid was spray dried and then re-hydrated using deionized water. The concentrations of phytoglycogen and oil in the re-hydrated liquid sample are given below.

No. 1: phytoglycogen from heat-treated (110° C., 4 hours), degermed kernels, subjected to ultrafiltration using tangential flow filtration (TFF) system. Phytoglycogen concentration was 5% w/w.

No. 2: emulsion stabilized with phytoglycogen from heat-treated (110° C., 4 hours), degermed kernels, phytoglycogen extraction subjected to ultrafiltration. Phytoglycogen concentration was 3.3% w/w, and oil concentration was 1.7% w/w.

No. 3: emulsion stabilized with phytoglycogen from heat-treated (110° C., 4 hours), non-degermed kernels, phytoglycogen extraction subjected to ultrafiltration. Phytoglycogen concentration was 3.3% w/w, and oil concentration was 1.7% w/w.

No. 4: emulsion stabilized with phytoglycogen from heat-treated (110° C., 24 hours), non-degermed kernels, subjected to TFF treatment. Phytoglycogen concentration was 3.3% w/w, and oil concentration was 1.7% w/w.

No. 5: emulsion stabilized with phytoglycogen from heat-treated (110° C., 24 hours), degermed kernels, phytoglycogen extraction subjected to protease (Alphalase NP)

treatment and ultrafiltration. Phytoglycogen concentration was 3.75% w/w, and oil concentration was 1.25% w/w.

No. 6: phytoglycogen from heat-treated (110° C., 24 hours), non-degermed kernels, phytoglycogen extraction subjected to protease (Alphalase NP) treatment and ultrafiltration. Phytoglycogen concentration was 5% w/w.

Figure 4:
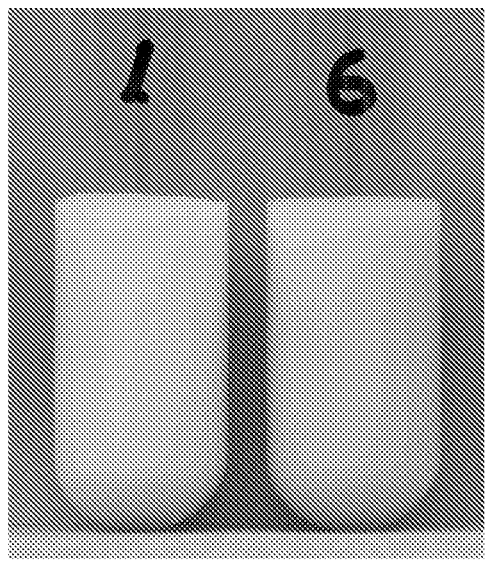

FIG. 4: Emulsions formed using re-hydrated phytoglycogen solid.

No. 1: the first emulsion described in Example 5, in which the phytoglycogen was extracted from heat-treated, degermed sweet corn kernels.

No. 6: the second emulsion described in Example 5, in which the phytoglycogen was extracted from heat-treated, non-degermed sweet corn kernels, and the phytoglycogen extraction was also subjected to protease treatment.

DETAILED DESCRIPTION

The present invention discloses that phytoglycogen functionality can be altered by enzymatic treatment, particularly the proteolytic hydrolysis. In addition, heating of phytoglycogen-containing materials, such as sweet corn kernels, can offer desirable functionalities. The resulted functionalities include enhanced emulsion stability, which is highly desirable for materials used as, for example, the emulsifier of emulsions, wall materials for encapsulation, bulking agent in liquid, semi-solid, or solid food, creams for personal cares and other purposes, coatings, and delivery tools of bioactive compounds or other material for food, drug, and agricultural chemicals.

In contrast, untreated phytoglycogen materials usually show low capability to stabilize oil-in-water emulsion.

Exemplary Physical and Functional Attributes of the Present Materials.

The treated phytoglycogen materials possess enhanced capability to form and stabilize oil-in-water emulsions, either by alone (i.e. phytoglycogen material-only, no other emulsifier) or in conjunction with other types of emulsifier (such as whey protein or gum Arabic) or stabilizers (such as xanthan gum or pectin), in comparison with untreated phytoglycogen materials.

The materials can be phytoglycogen-containing materials, or any materials that contain the analogues of phytoglycogen, such as glycogen or glycogen-type materials from animal, microorganisms, and plants.

Alternate Embodiments of the Methods of the Present Invention

Protease treatment can be applied before or after purification procedures, such as solvent precipitation or ultrafiltration.

In addition, protease treatment can be conducted simultaneously with the ultrafiltration process.

To extract phytoglycogen materials, various plant materials can be used, such as kernels of sweet corn or sweet rice. For su1-containing sweet corn (commercially available), phytoglycogen can be extracted using various methods, such as (1) grinding followed by water extraction, (2) soaking followed by milling, (3) removal of germs followed by water extraction, and/or (4) other methods or procedures. The methods of phytoglycogen extraction do not incur any limitations to the present invention.

The starting materials, such as the kernels of su1-containing corn or sweet rice grains can be pre-treated to enhance the quality of phytoglycogen materials. The pre-treatment of kernels can be (1) heating the kernels or the grits or flours obtained by grinding the kernels, (2) soaking kernels with acidic, neutral, or basic solutions and then dehydrating or milling, and (3) steaming kernels or the grits or flours obtained by grinding the kernels. In general, the kernels or their size-reduced materials, regardless the application of pre-treatments, are referred as "starting materials" and included in the present invention.

Purification of phytoglycogen materials may include (1) solvent precipitation, (2) ultrafiltration, (3) centrifugation or filtration, and (4) other methods to purify phytoglycogen. The methods of phytoglycogen purification do not incur any limitations to the present invention.

The present invention is further characterized by contacting protease(s), including proteolytic enzymes and/or peptide hydrolases, with phytoglycogen materials. The proteases can be plant, animal, and/or microorganism-derived. The protease can also be acidic, neutral, or alkaline proteases. A mixture of proteases can be used.

The proteases can also be used in combination with other types of enzymes, such as lipase or amylase, either separately or simultaneously.

Exemplary Embodiments of the Methods of the Present Invention

One method is characterized by using protease to treat phytoglycogen materials in conditions that are suitable for enhancing the capability of phytoglycogen-containing materials to maintain emulsion stability.

Another method is characterized by using heat treatment of plant materials that contain phytoglycogen, using conditions that are suitable for enhancing the capability of phytoglycogen-containing materials to maintain emulsion stability.

Another method is characterized by using both heat treatment and protease treatment of materials that contain phytoglycogen, using conditions that are suitable for enhancing the capability of phytoglycogen-containing material to maintain emulsion stability.

Each and all methods indicated above may also involve analogues of phytoglycogen, such as glycogen or glycogen-type materials from animal, microorganisms, or plants.

Exemplary Embodiments of the Uses of the Present Materials

Formation of emulsions using phytoglycogen materials and their analogues.

Use of phytoglycogen materials and their analogues in encapsulations.

Use of phytoglycogen materials and their analogues as bulking agent.

Use of phytoglycogen materials and their analogues in creams for cosmetics and personal cares.

Use of phytoglycogen materials and their analogues for protecting and/or delivering bioactive compounds, or other materials, such as antimicrobial peptides, polyphenol antioxidants, flavors, fragrances, or polyunsaturated fatty acids.

Use of phytoglycogen materials and their analogues to deliver agricultural chemicals, such as fungicide, herbicide, insecticide, plant nutrients, and/or fertilizers.

Use of phytoglycogen materials and their analogues in the coating of food, to improve the appearance, and/or to protect the food surface from moisture migration, oxidation, and/or growth of microorganism.

Use of phytoglycogen materials and their analogues in the coating of plant or plant-based materials such as seeds and leaves, to improve the appearance, and/or to protect the surface from moisture migration, oxidation, insects, and/or growth of microorganism.

EXAMPLES

Example 1

Effect of Protease Treatment

1A. Phytoglycogen Extraction.

One hundred grams of non-treated sweet corn kernels (Silver Queen Cultivar, Burpee) were ground to coarse powder, and then added with 300 mL of pre-cooled (4° C.) deionized water. The mixture was homogenized using a blender and pressed through a 270-mesh sieve. The solids were mixed with water for further extractions. The total water used was 1200 mL. The filtrates from sieve were pooled and subjected to 3 times of centrifugation (10,000×g, 30 min). For each time, the supernatant was filtered through the 270-mesh sieve to remove the cream layer. The final supernatants were collected.

1B. Protease Treatment.

A portion of phytoglycogen extraction from 1A was subjected to protease treatment using Alphalase NP (neutral proteolytic enzyme from Danisco-DuPont). For the enzymatic treatment, 200 mL of supernatant was warmed to 40° C., adjusted to pH 6.5, and then added with 20 μL enzyme. The reaction was continued for 2 hours and then the reactant was brought to boiling to denature the enzyme. The mixture was allowed to cool down.

1C. Ultrafiltration

Protease-treated phytoglycogen extraction from 1B was subjected to ultrafiltration using a bench-top TFF (tangential flow filtration) system (Minimate, Pall Life Sciences). The conditions were: membrane molecular weight cut-off (MWCO) 300 k Da, pressure 20-30 psi. For the TFF operation, the total volume of feed was reduced from 150 mL to 50 mL, added with 50 mL water, and then reduced to 50 mL again. Thereafter, 50 mL water was added to retentate and the volume was again reduced to 50 mL. 50 mL water was again added and the volume was eventually reduced to 20 mL.

As the reference, non-protease-treated phytoglycogen extraction was also subjected to ultrafiltration in the same procedure.

1D. Emulsification.

Phytoglycogen dispersions from 1C (with phytoglycogen of about 7.5% w/w) were added with soybean oil (50% of phytoglycogen weight), subjected to vortex and then the high-pressure homogenization (Nano DeBee, BEE International) with 138 MPa for 3 cycles. The emulsions collected were placed in refrigerator (4° C.) for stability tests.

1E. Emulsion Stability.

Emulsions from 1D were stored in a refrigerator for 2 days and then observed. The emulsion formed by non-protease-treated phytoglycogen dispersion showed evident cream layer separation, indicating the low capability of non-protease-treated phytoglycogen as emulsifier. In contrast, the emulsion formed by protease-treated phytoglycogen showed negligible layer separation, indicating the high capability of protease-treated phytoglycogen as emulsifier to stabilize oil-in-water emulsion.

Example 2

Effect of Heat Treatment of Degermed Corn Kernels

2A. Heat Treatment.

About 70 grams of degermed sweet corn kernels was heated at 110° C. in a ventilated oven for 4 hours and then allowed to cool to room temperature.

2B. Phytoglycogen Extraction

Sixty-seven grams of heat-treated, degermed corn kernels were ground to coarse powder, and then added with 300 mL of pre-cooled (4° C.) deionized water. The mixture was homogenized using a blender and pressed through a 270-mesh sieve. The filtrates from sieve were subjected to centrifugation (10,000×g, 30 min). The supernatant was filtered through the 270-mesh sieve to remove the cream layer. The liquid was collected.

Sixty-seven grams of non-heated, degermed corn kernels were subjected to the same procedure as described for heat-treated, degermed kernels.

2C. Ultrafiltration.

Phytoglycogen extraction from heat-treated, degermed corn kernels was subjected to ultrafiltration using a bench-top TFF in a similar procedure as described in Example 1, that is, the dispersion was subjected to repetitive ultrafiltration and addition of water to the retentate in a TFF system, using a membrane with MWCO of 300 k Da. The phytoglycogen extraction from non-heated, degermed corn kernels was subjected to the same ultrafiltration procedure.

2D. Emulsification.

Each of phytoglycogen dispersions from 2C (with phytoglycogen of about 10.5% w/w) was added with soybean oil (50% of phytoglycogen weight), subjected to vortex and then the high-pressure homogenization (Nano DeBee) with 138 MPa for 3 cycles. The emulsions collected were placed in refrigerator (4° C.).

2E. Emulsion Stability.

After 9 days storage in the refrigerator, the emulsion formed in 3C was photographed. The result is shown in FIG. 1. Heat treatment of kernels led to a phytoglycogen-containing material with strong capability to stabilize emulsion. In contrast, kernels without heat treatment led to a phytoglycogen-containing material with low capability to stabilize emulsion.

Example 3

Effect of Heat Treatment of Non-Degermed Corn Kernels

3A. About 200 grams of non-degermed sweet corn kernels (Silver Queen cultivar, Burpee) were heated at 110° C. in a ventilated oven for 4 or 24 hours and then allowed to cool to room temperature.

3B. Sixty grams of heat-treated (4 or 24 hours), non-degermed corn kernels were soaked in water in a 4° C. refrigerator for 48 hours. Thereafter, the soaking water was removed and fresh water was added to a total volume of 200 mL containing swollen kernels. The mixture was then treated using a blender to disrupt the kernels to release phytoglycogen. After filtration using a 270-mesh sieve, the solid was further extracted using additional 400 mL water. The mixture was filtered again and all liquid portions were pooled. The liquid was then subjected to centrifugation (10,000×g, 30 min). The supernatant was filtered through the 270-mesh sieve to remove the cream layer. The liquid was collected. The non-heated, non-degermed corn kernels were subjected to the same procedure.

3C. Ultrafiltration.

Phytoglycogen extractions from heat-treated, non-degermed corn kernels (described in 3A and 3B) were subjected to ultrafiltration using a bench-top TFF in a similar procedure as described in Example 1, that is, the dispersion was subjected to repetitive ultrafiltration and addition of water to the retentate in the TFF system, using a membrane with MWCO of 300 k Da. The phytoglycogen extraction from non-heated, non-degermed corn kernels was subjected to the same ultrafiltration procedure.

3D. Emulsification.

Phytoglycogen dispersions from 3C (with phytoglycogen of about 7.5% w/w) was added with soybean oil (50% of phytoglycogen weight), subjected to vortex and then the high-pressure homogenization (Nano DeBee) with 138 MPa for 2 cycles. The emulsions collected were placed in a refrigerator (4° C.).

3E. Emulsion Stability.

After 5 days storage in the refrigerator, the emulsion formed in 3D was photographed. The result is shown in FIG. 2. Heat treatment led to an outstanding emulsion stability of phytoglycogen, as compared with that without heat treatment.

Example 4

Spray Drying and Re-Hydration of Phytoglycogen Dispersion and the Emulsion Stabilized Using Phytoglycogen 4A. Spray Drying.

Phytoglycogen dispersions and phytoglycogen-stabilized oil-in-water emulsions were subjected to spray drying (Lab-Plant Spray Dryer SD-06, Keison International). The conditions were: inlet air temperature 150° C., outlet air temperature 90° C., air blow 058, and pump speed 0.06. Fine powders were obtained for all samples.

4B. Re-Hydration.

To each spray-dried solid (in the powder form) 0.25 grams, 5 mL deionized water was added and the mixture was subjected to vortex. For each sample, a homogenous dispersion or emulsion was immediately formed, showing the effective re-hydration of spray dried phytoglycogen materials and phytoglycogen-stabilized emulsions. The results are shown in FIG. 3.

Example 5

Stability of Emulsions Formed Using Re-Hydrated Phytoglycogen

5A. Preparation of Emulsion.

The first phytoglycogen-stabilized emulsion was prepared through the following procedure: (1) subjecting degermed kernels of sweet corn (Silver Queen Cultivar, Burpee) to heat-treatment (110° C., 4 hours), (2) extracting phytoglycogen from treated kernels, (3) treating phytoglycogen extraction with ultrafiltration using a tangential flow filtration (TFF) system, (4) spray drying purified phytoglycogen into a solid powder, (5) re-dispersing phytoglycogen powder using deionized water, forming a dispersion of 5% (w/w) phytoglycogen, (6) adding soybean oil (50% of phytoglycogen weight) in the dispersion, (7) subjecting the mixture to a high pressure homogenizer (Nano DeBee, BEE International) at approximately 138 MPa for 3 cycles to form emulsions. The emulsion was then stored at a 4° C. refrigerator.

The second phytoglycogen-stabilized emulsion was prepared through the following procedure: (1) subjecting non-degermed kernels of sweet corn (Silver Queen Cultivar, Burpee) to heat-treatment (110° C., 24 hours), (2) extracting phytoglycogen from treated kernels, (3) treating phytoglycogen extraction using a neutral protease, Alphalase NP (Danisco-DuPont) for 2 hours followed by boiling to deactivate enzyme, (4) treating collected phytoglycogen extraction with ultrafiltration using a tangential flow filtration (TFF) system, (5) spray drying purified phytoglycogen into a solid powder, (6) re-dispersing phytoglycogen powder using deionized water, forming a dispersion of 2.5% phytoglycogen, (7) adding soybean oil (50% of phytoglycogen weight) in the dispersion, (8) subjecting the mixture to a high pressure homogenizer (Nano DeBee, BEE International) at approximately 138 MPa for 2 cycles to form emulsions. The emulsion was then stored at a 4° C. refrigerator.

5B. Emulsion Stability.

The emulsions prepared in 5A were stored at a 4° C. refrigerator for 1 day and then photographed. The outcome is shown in FIG. 4. It is evident that the both emulsions were highly stable, without observable formation of cream layers, flocculation and coalescence. This indicates the high capability of re-hydrated, treated phytoglycogen materials to maintain the stability of emulsion.

Example 6

Lotion Stability

Phytoglycogen was extracted using deionized water from non-degermed, heat-treated (105° C., 4 hours) sweet corn kernels. After centrifugation to remove insoluble materials, the liquid phytoglycogen extraction was added to 4 volumes of pure ethanol, followed by repetitive washing using ethanol to dehydrate. The precipitate collected was placed in fume hood to remove residual ethanol and solid powder of phytoglycogen material was obtained. Phytoglycogen material was also obtained from non-degermed, non-heated kernels as the reference.

The phytoglycogen materials were used in lotion emulsion formulation, which contains mineral oil 5%, cetyl stearyl alcohol 3%, methyl p-hydroxybenzoate 0.1%, phytoglycogen 5%, and deionized water 86.9%. High pressure homogenization was conducted using a two-stage homogenizer (PandaPlus 2000, GEA Niro Soavi) at about 1000 bar with two cycles. The emulsions formed were placed at room temperature for observation. The result indicated that the phytoglycogen material extracted from the heat-treated kernels led to a significantly more stable emulsion than the emulsion formed by the phytoglycogen material extracted from non-heated kernels. In comparison, emulsion could not be formed without the addition of phytoglycogen material.

What is claimed is:

1. A method for making a phytoglycogen composition with emulsification attributes, comprising subjecting a phytoglycogen-containing material to at least one heat treatment under conditions sufficient to obtain a phytoglycogen composition having at least one emulsification attribute, wherein the phytoglycogen-containing material is heat treated when the material moisture content is from approximately 0% to 40%, and further comprising enhancing the content of phytoglycogen in the phytoglycogen containing material.

2. The method of claim 1, wherein the at least emulsification attribute exists by the phytoglycogen composition alone.

3. The method of claim 1, wherein the at least one emulsification attribute is selected from a group of capabilities consisting of: forming emulsions with unobservable or negligible cream layer formation; forming emulsions with unobservable or negligible layer separation; forming emulsions with unobservable or negligible flocculation; forming emulsions with unobservable or negligible coalescence; and/or forming emulsions with overall homogeneity during storage.

4. The method of claim 1, wherein the at least one emulsification attribute is that the emulsion is stable for at least 10 minutes.

5. The method of claim 1, wherein the at least one emulsification attribute is the stability of emulsion formed by treated phytoglycogen composition higher than the stability of emulsion formed by untreated control phytoglycogen-containing material, wherein said stability increase percentage is at least about 30%.

6. The method of claim 1, wherein the phytoglycogen-containing material is heat treated when the material moisture content is from approximately 0% to 20%.

7. The method of claim 1, wherein the phytoglycogen-containing material is heat treated for at least approximately 5 seconds.

8. The method of claim 1, wherein the phytoglycogen-containing material is heat treated at a temperature of at least approximately 30° C.

9. The method of claim 1, which further comprises subjecting the phytoglycogen-containing material to protease treatment.

10. The method of claim 1, which further comprises one or more treatments selected from the group consisting of: enzyme treatment, protease treatment, extraction, purification, spray drying; freeze drying; drum drying; chemical substitution; emulsifying; and ingredient use.

11. A phytoglycogen composition having at least one emulsification attribute prepared by a process comprising the step of subjecting a phytoglycogen-containing material to at least one heat treatment, under conditions sufficient to obtain a phytoglycogen composition having at least one emulsification attribute, wherein the phytoglycogen-containing material is heat treated when the material moisture content is from approximately 0% to 40%, and further comprising enhancing the content of phytoglycogen in the phytoglycogen containing material.

12. The phytoglycogen composition of claim 11, wherein the composition is in the form selected from the group consisting of: a microparticle; a nanoparticle; a powder; a granule; a solid; a liquid; a semi-solid; an emulsion; a mixture; a coating; a packaging material; and a cake.

13. A product comprising a phytoglycogen composition having at least one emulsification attribute prepared by a process comprising the step of subjecting a phytoglycogen-containing material to at least one heat treatment, under conditions sufficient to obtain a phytoglycogen composition having at least one emulsification attribute, wherein the phytoglycogen-containing material is heat treated when the material moisture content is from approximately 0% to 40%, and further comprising enhancing the content of phytoglycogen in the phytoglycogen containing material.

14. The product of claim 13, which is selected from the group consisting of: a food, a food ingredient, food packaging, beverage, beverage mix, ready-to-eat cereal, ready-to-eat snack piece, nutritional supplement, flavor and fragrance, dairy product, confection, baked good, soup, topping, sauce, processed meat product, vegetarian product, frozen food, coating materials, encapsulation materials, micro-encapsulation materials, packaging materials, antimicrobial materials, anti-oxidation materials, and edible decoration.

15. The product of claim 13, which is selected from the group consisting of: a cosmetic, cream, lotion, foundation, eyeliner, rouge, wrinkle modifier, blemish concealer, nail product, skin colorant, mask, lipstick, mascara, moisturizer, sunscreen, anti-wrinkle lotion, antibiotic lotion, muscle pain lotion, foot cream, body lotion, medical lotion, hand cream, stretch mark cream, hair treatment, shampoo, conditioner, cream rinse, shining product, holding product, color product, straightening product, and curling product.

16. The product of claim 13, which is selected from the group consisting of: a pharmaceutical, nutraceutical, supplement, a capsule, tablet, liquid, gel, ointment, intravenous formulation, lotion, transdermal delivery formulation, toothpaste, dental treatment, inhalant, medical food, and injectable.

17. The method of claim 1, wherein the at least one emulsification attribute exists by the phytoglycogen composition in conjunction with other materials.

18. The method of claim 1, wherein the at least one emulsification attribute is that the emulsion formed is stable for at least 100 minutes.

19. The method of claim 1, wherein the at least one emulsification attribute is that the emulsion formed is stable for at least 1,000 minutes.

20. The method of claim 1, wherein the at least one emulsification attribute is that the emulsion formed is stable for at least 10,000 minutes.

21. The method of claim 1, wherein the at least one emulsification attribute is the stability of emulsion formed by treated phytoglycogen composition higher than the stability of emulsion formed by untreated control phytoglycogen-containing material, wherein said stability increase percentage is at least about 100%.

22. The method of claim 1, wherein the at least one emulsification attribute is the stability of emulsion formed by treated phytoglycogen composition higher than the stability of emulsion formed by untreated control phytoglycogen-containing material, wherein said stability increase percentage is at least about 1,000%.

23. The method of claim 1, wherein the at least one emulsification attribute is the stability of emulsion formed by treated phytoglycogen composition higher than the stability of emulsion formed by untreated control phytoglycogen-containing material, wherein said stability increase percentage is at least about 10,000%.

24. The method of claim 1, wherein the phytoglycogen-containing material is heat treated at a temperature of at least approximately 50° C.

* * * * *